(12) United States Patent
Kang et al.

(10) Patent No.: US 12,331,283 B2
(45) Date of Patent: Jun. 17, 2025

(54) ***BIFIDOBACTERIUM ANIMALIS* SUBSP. *LACTIS* GFC-B09 STRAIN AND COSMETIC COMPOSITION CONTAINING SAME**

(71) Applicant: GFC Life Science CO., Ltd., Hwaseong-si (KR)

(72) Inventors: Hee Cheol Kang, Seoul (KR); Mi Yeon Cha, Yongin-si (KR); Mi An, Suwon-si (KR); Yeon Sun Jung, Suwon-si (KR); Jeong Ran Heo, Yongin-si (KR)

(73) Assignee: GFC Life Science CO., Ltd., Hwaseong-si (KR)

( * ) Notice: Subject to any disclaimer, the term of this patent is extended or adjusted under 35 U.S.C. 154(b) by 292 days.

(21) Appl. No.: 18/052,975

(22) Filed: Nov. 7, 2022

(65) Prior Publication Data
US 2023/0193196 A1    Jun. 22, 2023

Related U.S. Application Data

(63) Continuation of application No. 16/832,928, filed on Mar. 27, 2020, now abandoned.

(30) Foreign Application Priority Data

Mar. 29, 2019  (KR) .......................... 10-2019-0036785

(51) Int. Cl.
| | | |
|---|---|---|
| *A61Q 19/00* | (2006.01) | |
| *A61K 8/99* | (2017.01) | |
| *C12N 1/20* | (2006.01) | |
| *C12R 1/01* | (2006.01) | |

(52) U.S. Cl.
CPC ................ *C12N 1/205* (2021.05); *A61K 8/99* (2013.01); *A61Q 19/00* (2013.01); *C12N 1/20* (2013.01); *C12R 2001/01* (2021.05)

(58) Field of Classification Search
CPC . C12N 1/205; C12N 1/20; A61K 8/99; A61K 2800/85; A61Q 19/00; A61Q 19/08; A61Q 19/02; C12R 2001/01
See application file for complete search history.

(56) References Cited

U.S. PATENT DOCUMENTS

2021/0121507 A1 * 4/2021 Bogicevic ................ A61P 1/00

FOREIGN PATENT DOCUMENTS

| EP | 1974719 A1 * | 10/2008 | ............. A61K 35/12 |
|---|---|---|---|
| KR | 20170010270 A * | 1/2017 | |
| KR | 10-1788544 B1 | 10/2017 | |
| KR | 10-1802963 B1 | 11/2017 | |
| KR | 10-1958686 B1 | 3/2019 | |

OTHER PUBLICATIONS

Mattila-Sandholm, et. al. Probiotics: towards demonstrating efficacy, 1999, Trends in Food Science & Technology, 10: 393-399 (Year: 1999).*
FARE, Food Allergy Research and Education, Jul. 2024, https://www.foodallergy.org/resources/food-allergy-myths-and-facts (Year: 2024).*
Masco, L et al. Polyphasic taxonomic analysis of Bifidobacterium animalis and Bifidobacterium lactis, 2004, International Journal of Systematic and Evolutionary Microbiology, 54(4): 1137-1143 (Year: 2004).*
"Food Microbiology Testing Techniques", Zeng Yangqing Editor-in-Chief, Chengdu: Southwest Jiaotong University Press, Jan. 31, 2016.

* cited by examiner

*Primary Examiner* — Louise W Humphrey
*Assistant Examiner* — Anjali Ajit Hirani
(74) *Attorney, Agent, or Firm* — NKL Law; Jae Youn Kim

(57) ABSTRACT

Provided is a *Bifidobacterium animalis* subsp. *Lactis* GFC-B09 strain and a cosmetic composition containing the same. The *Bifidobacterium animalis* subsp. *Lactis* GFC-B09 strain (Accession number: KCCM12263P) or a culture solution thereof has the ability to increase the amount of *S. epidermidis*, to degrade histamine, to inhibit allergies, to repair DNA, and to increase wrinkle resistance, skin whiteness, skin density, and skin elasticity, and thus can exhibit excellent effects as a cosmetic composition when contained as an active ingredient in a cosmetic base.

4 Claims, 8 Drawing Sheets

Specification includes a Sequence Listing.

FIG. 1

SEQUENCE LISTING

```
Sequence total quantity: 6
SEQ ID NO: 1            moltype = DNA  length = 20
FEATURE                 Location/Qualifiers
misc_feature            1..20
                        note = Universal primer 27F
source                  1..20
                        mol_type = other DNA
                        organism = synthetic construct
SEQUENCE: 1
agagtttgat cmtggctcag                                                 20

SEQ ID NO: 2            moltype = DNA  length = 22
FEATURE                 Location/Qualifiers
misc_feature            1..22
                        note = Universal primer 1492R
source                  1..22
                        mol_type = other DNA
                        organism = synthetic construct
SEQUENCE: 2
tacggytacc ttgttacgac tt                                              22

SEQ ID NO: 3            moltype = DNA  length = 1481
FEATURE                 Location/Qualifiers
misc_feature            1..1481
                        note = Bifidobacterium sp. GFC B09
source                  1..1481
                        mol_type = other DNA
                        organism = synthetic construct
SEQUENCE: 3
gggcgtgggg gtcgtgctta ccatgcagtc gaacgggatc cctggcagct tgctgtcggg     60
gtgagagtgg cgaacgggtg agtaatgcgt gaccaacctg ccctgtgcac cggaatagct    120
cctgaaacg ggtggtaata ccggatgctc cgctccatcg catggtgggg tgggaaatgc     180
ttttgcggca tgggatgggg tcgcgtccta tcagcttgtt ggcggggtga tggcccacca    240
aggcgttgac gggtagccgg cctgagaggg tgaccggcca cattgggact gagatacggc    300
ccagactcct acgggaggcc agccagtggg ggaattattg ccacaatggg gcgccaagcc    360
ctgaatgcaa gcgaccgccg gcgtgccggg gatgaaggc ctttcggggt tgtaaacccg     420
cttttggttc aagggccaag gccacggttt tcggcccgtg ttgaattgga ttgtttcgaa    480
ttagcacccg gctaactacg tgccagcagc cgcgtaatca cgtaggggtg cgagcgttat    540
cccggattta ttgggcgtaa aggggctcgt aggcggttcg tcgcgtcccg gtgtgaaagt    600
ccatcgccta acggtggatc tgcgccgggt acgggcgggc tggagtgcgg taggggagac    660
tggaattccc ggtgtaacgg tggaatgtgt agatatcggg aagaacacca atggcgaagg    720
caggtctctg ggccgtcact gacgctgagg agcgaaagcg tggggagcga acaggattag    780
atacccctggt agtccacgcc gtaaacgtg gatgctggat gtgggccct ttccacgggt     840
cccgtgtcgg agccaacgcg ttaagcatcc gcctgggga gtacggccgc aaggctaaaa    900
ctcaaagaaa ttgacggggg cccgcacaag cggcggagca tgcggattaa ttcgatgcaa    960
cgcgaagaac cttacctggg cttgacatgt gccggatcgc cgtggagaca cggtttccct   1020
tcggggccgg ttcacaggtg gtgcatggtc gtcgtcagct cgtgtcgtga gatgttgggt   1080
taagtcccgc aacgagcgca accctcgccg catgttgcca gcgggtgatg ccgggaactc   1140
atgtgggacc gccggggtca actcggagga aggtggggat gacgtcagat catcatgccc   1200
```

```
cttacgtcca gggcttcacg catgctacaa tggccggtac aacgcggtgc gacacggtga 1260
cgtgggggcgg atcgctgaaa accggtctca gttcggatcg cagtctgcaa ctcgactgcg 1320
tgaaggcgga gtcgctagta atcgcggatc agcaaccgccg cggtgaatgc gttcccgggc 1380
cttgtacaca ccgcccgtca agtcatgaaa gtgggtagca cccgaagccg gtggcccgac 1440
ccttgtgggg ggagccgtct aatgatagat ctccgaggtc t                     1481

SEQ ID NO: 4           moltype = DNA  length = 40
FEATURE                Location/Qualifiers
misc_feature           1..40
                       note = GC clamp
source                 1..40
                       mol_type = other DNA
                       organism = synthetic construct
SEQUENCE: 4
cgcccggggc gcgccccggg cggggcgggg gcacgggggg                                40

SEQ ID NO: 5           moltype = DNA  length = 17
FEATURE                Location/Qualifiers
misc_feature           1..17
                       note = 341F
source                 1..17
                       mol_type = other DNA
                       organism = synthetic construct
SEQUENCE: 5
cctacgggag gcagcag                                                         17

SEQ ID NO: 6           moltype = DNA  length = 17
FEATURE                Location/Qualifiers
misc_feature           1..17
                       note = 518R
source                 1..17
                       mol_type = other DNA
                       organism = synthetic construct
SEQUENCE: 6
attaccgcgg ctgctgg                                                         17
```

BIFIDOBACTERIUM ANIMALIS SUBSP. LACTIS GFC-B09 STRAIN AND COSMETIC COMPOSITION CONTAINING SAME

CROSS-REFERENCE TO RELATED APPLICATION

The application is a continuation of U.S. patent application Ser. No. 16/832,928, filed Mar. 27, 2020, which claims priority to Korean Patent Application No. 10-2019-0036785, filed on Mar. 29, 2019, the entire content of each is incorporated herein for all purposes by this reference.

INCORPORATION OF SEQUENCE LISTING

This application contains a sequence listing submitted in Computer Readable Form (CRF). The CRF file containing the sequence listing entitled "PK3803815CON.xml", which was created on Nov. 4, 2022, and is 9,980 bytes in size. The information in the sequence listing is incorporated herein by reference in its entirety.

BACKGROUND OF THE INVENTION

1. Technical Field

The present invention relates to a *Bifidobacterium animalis* subsp. *Lactis* GFC-B09 strain and a cosmetic composition containing the same.

2. Description of the Related Art

The skin ecosystem provides microorganisms with a variety of habitats and a wide range of microorganisms live thereon. The host person has a symbiotic relationship with such microorganisms, which is known to have many beneficial effects for the host. The skin forms a variety of habitats, including indentations, specialized niches, etc., promoting the growth of a wide range of microorganisms. Basically, the skin forms a physical membrane, and helps to defend against potential hazards and toxins from the outside. The skin is the point of contact with the external environment and is a collection place for various microorganisms (fungi, bacteria, viruses and small larvae). Depending on the respective physical and chemical functions thereof, the microorganisms adapt to specialized niches and provide habitats. In general, the skin is cold, acidic and remains dry. Structurally, the epidermis forms the skin barrier, and plays an important role in blocking the penetration of microorganisms and toxins and maintaining moisture. The outermost layer of the epidermis is composed of the stratum corneum, and is differentiated from keratinocytes. The epidermis has a form called a "brick and mortar structure". The skin tissue undergoes a continuous self-healing process, and the squames resulting from the end of the differentiation process are repeatedly detached from the skin tissue.

Meanwhile, bacteria that ferment sugars to obtain energy and generate a large amount of lactic acid are collectively called lactic acid bacteria. Lactic acid bacteria live in the intestine in symbiosis with the digestive system of the human body and break down fiber and complex proteins into important nutrients.

In addition, by keeping the intestinal environment acidic, lactic acid bacteria inhibit the growth of harmful bacteria, alleviate diarrhea and constipation and are responsible for vitamin synthesis and blood cholesterol inhibition. Lactic acid bacteria are able to strongly bind to intestinal mucosa and epithelial cells, which is greatly helpful for intestinal action and enhances the activity of macrophages and the spleen to thus secrete and promote substances involved in immune responses. Moreover, these also have an immune regulatory function, and are thus effective in atopy and allergy-related diseases.

In the field of cosmetics, lactic acid bacteria cultures have been used since first commercialized in 1955 and are still used at present. Thorough research has been carried out into filtration or extraction after direct fermentation of a culture solution or after fermentation through seeding with an active material mainly using *Streptococcus* genus, *Lactobacillus* genus, *Lactococcus* genus, *Leuconostoc* genus, *Bifidobacterium* genus, etc.

In particular, as techniques for various applications using *Bifidobacterium* genus, Korean Patent No. 10-1958686 discloses a composition containing *Bifidobacterium animalis* ssp. *lactis* HY8002 as an active ingredient for preventing from skin damage and improving skin health in the presence of fine dust, Korean Patent No. 10-1788544 discloses a cosmetic composition containing a mixed lactic acid bacteria culture for enhancing the skin barrier, and Korean Patent No. 10-1802963 discloses a cosmetic composition using fermented extracts.

Looking again at the ecological environment of the skin, the physical and biological elements may be harmonized to provide a variety of habitats, and there is also a need to think about the delicate balance between humans and microorganisms. When the symbiotic balance is broken, the skin breaks down and is easily infected.

Therefore, the present inventors have discovered that the isolated and identified novel *Bifidobacterium* sp. GFC-B09 strain (Accession number: KCCM12263P) has the ability to increase the amount of *S. epidermidis*, which is a skin-microbiome strain, to degrade histamine, to inhibit allergies, to repair DNA, and to increase wrinkle resistance, skin whiteness, skin density, and skin elasticity, thus culminating in the present invention.

SUMMARY OF THE INVENTION

An objective of the present invention is to provide a novel strain having the ability to increase the amount of *S. epidermidis*, which is a skin-microbiome strain, to degrade histamine, to inhibit allergies, to repair DNA, and to increase wrinkle resistance, skin whiteness, skin density, and skin elasticity.

Another objective of the present invention is to provide a method of manufacturing a culture solution including seeding a novel strain into an MRS medium and performing culturing and a culture solution manufactured thereby.

Still another objective of the present invention is to provide a cosmetic composition containing a novel strain or a culture solution thereof as an active ingredient.

In order to accomplish the above objectives, the present invention provides a *Bifidobacterium animalis* subsp. *Lactis* GFC-B09 strain (Accession number: KCCM12263P), having the ability to increase the amount of *S. epidermidis*, which is a skin-microbiome strain, to degrade histamine, to inhibit allergies, to repair DNA, and to increase wrinkle resistance, skin whiteness, skin density, and skin elasticity.

In the present invention, the strain may be derived from *Bombus pascuorum*.

In addition, the present invention provides a method of manufacturing a culture solution including seeding a *Bifi*- dobacterium animalis subsp. *Lactis* GFC-B09 strain (Accession number: KCCM12263P) into an MRS medium and performing culturing.

In the present invention, the culturing may be performed at 32-37° C. for 90-130 hr.

In addition, the present invention provides a culture solution obtained by culturing a *Bifidobacterium animalis* subsp. *Lactis* GFC-B09 strain (Accession number: KCCM12263P).

In addition, the present invention provides a cosmetic composition containing a *Bifidobacterium animalis* subsp. *Lactis* GFC-B09 strain (Accession number: KCCM12263P) or a culture solution thereof as an active ingredient.

In the present invention, the cosmetic composition may have the ability to increase the amount of *S. epidermidis*, to degrade histamine, to inhibit allergies, to repair DNA, and to increase wrinkle resistance, skin whiteness, skin density, and skin elasticity.

According to the present invention, a *Bifidobacterium animalis* subsp. *Lactis* GFC-B09 strain (Accession number: KCCM12263P) or a culture solution thereof has the ability to increase the amount of *S. epidermidis*, to degrade histamine, to inhibit allergies, to repair DNA, and to increase wrinkle resistance, skin whiteness, skin density, and skin elasticity, and thus can exhibit excellent effects as a cosmetic composition when contained as an active ingredient in a cosmetic base.

BRIEF DESCRIPTION OF DRAWINGS

FIG. 1 shows the nucleotide sequence (SEQ ID NO: 3) of a *Bifidobacterium animalis* subsp. *Lactis* GFC-B09 strain (Accession number: KCCM 12263P) according to the present invention;

DESCRIPTION OF SPECIFIC EMBODIMENTS

Figure 2:
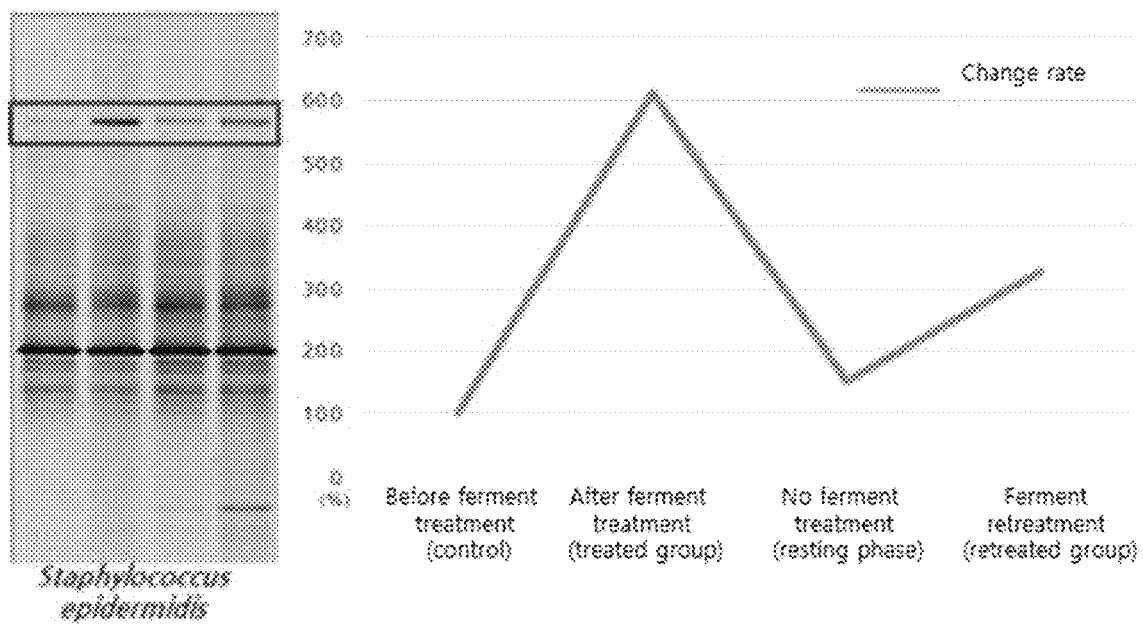
FIG. 2 shows changes in the amount of *S. epidermidis* when treating the skin with the culture solution of the *Bifidobacterium animalis* subsp. *Lactis* GFC-B09 strain (Accession number: KCCM 12263P) according to the present invention.

In the present invention, a strain having the ability to increase the amount of *S. epidermidis*, to degrade histamine, to inhibit allergies, to repair DNA, and to increase wrinkle resistance, skin whiteness, skin density, and skin elasticity was selected through screening of strains isolated from *Bombus pascuorum*, and was identified to be a novel microorganism belonging to the *Bifidobacterium* genus through 16s rRNA sequencing. Accordingly, it was named as a *Bifidobacterium* sp. GFC-B09 strain and was deposited on May 21, 2018 at the Korean Culture Center of Microorganisms.

Therefore, the present invention pertains to a *Bifidobacterium animalis* subsp. *Lactis* GFC-B09 strain (Accession number: KCCM12263P) (hereinafter abbreviated as 'GFC-B09') having the ability to increase the amount of *S. epidermidis*, to degrade histamine, to inhibit allergies, to repair DNA, and to increase wrinkle resistance, skin whiteness, skin density, and skin elasticity.

Here, the GFC-B09 strain is derived from *Bombus pascuorum*.

In addition, the present invention pertains to a method of manufacturing a culture solution including seeding a GFC-B09 strain into an MRS medium and performing culturing.

For culturing, a typical medium may be used. In particular, an MRS medium (10 g of proteose peptone No. 3, 10 g of beef extract, 5 g of yeast extract, 20 g of dextrose, 1 g of polyoxyethylene sorbitan monooleate, 2 g of ammonium citrate, 0.1 g of magnesium sulfate, 0.05 g of manganese sulfate, 2 g of dipotassium phosphate, 5 g/L of sodium acetate, pH 6.5) is preferably used because the yield of a culture solution may be most effectively increased through fermentation using the same.

The GFC-B09 strain is seeded in an amount of 1-3% at $1.0 \times 10^7$ to $1.0 \times 10^9$ into an MRS liquid medium, followed by culturing, particularly stationary culturing under anaerobic conditions at 32-37° C. for 90-130 hr. If the culturing temperature and time fall out of the above ranges, the conditions are unsuitable for culturing a fermentation strain, and thus the ability to increase the amount of *S. epidermidis*, to degrade histamine, to inhibit allergies, to repair DNA, and to increase wrinkle resistance, skin whiteness, skin density, and skin elasticity is not exhibited, or the strain does not proliferate, which is undesirable.

As described above, the culture solution may be manufactured in a manner in which the cultured strain is filtered at a pH of 3.8-4.2 and is then aged at 20-30° C. for 10-16 days.

In addition, the present invention pertains to a culture solution obtained by culturing a *Bifidobacterium animalis* subsp. *Lactis* GFC-B09 strain (Accession number: KCCM12263P).

The culture solution has the ability to increase the amount of *S. epidermidis*, to degrade histamine, to inhibit allergies, to repair DNA, and to increase wrinkle resistance, skin whiteness, skin density, and skin elasticity, and thus may exhibit excellent effects when used as a cosmetic composition.

Thus, the present invention pertains to a cosmetic composition containing, as an active ingredient, a *Bifidobacte-*

*rium animalis* subsp. *Lactis* GFC-B09 strain (Accession number: KCCM12263P) or a culture solution thereof.

The cosmetic composition according to the present invention may be provided in the form of a formulation selected from the group consisting of an external skin ointment, cream, softening skin lotion, nourishing skin lotion, pack, essence, hair tonic, shampoo, rinse, hair conditioner, hair treatment, gel, skin lotion, skin softener, skin toner, astringent, lotion, milk lotion, moisture lotion, nutrition lotion, massage cream, nutrition cream, eye cream, moisture cream, hand cream, foundation, nutrition essence, sunscreen, soap, cleansing foam, cleansing lotion, cleansing cream, body lotion and body cleanser, but is not limited thereto. The composition of each formulation may contain a variety of bases and additives necessary and suitable for the preparation of the formulation, and the types and amounts of these components may be easily selected by those skilled in the art.

When the formulation of the present invention is a paste, cream or gel, animal fiber, plant fiber, wax, paraffin, starch, tragacanth, cellulose derivative, polyethylene glycol, silicone, bentonite, silica, talc, zinc oxide or the like may be used as a carrier component.

When the formulation of the present invention is a powder or spray, lactose, talc, silica, aluminum hydroxide, calcium silicate or polyamide powder may be used as a carrier component. In the case of spray in particular, it may additionally contain a propellant such as chlorofluorohydrocarbon, propane/butane or dimethyl ether.

When the formulation of the present invention is a solution or emulsion, a solvent, a solvating agent or an emulsifying agent may be used as a carrier component, and examples thereof may include water, ethanol, isopropanol, ethyl carbonate, ethyl acetate, benzyl alcohol, benzyl benzoate, propylene glycol, 1,3-butylglycol oil, glycerol aliphatic ester, polyethylene glycol or sorbitan fatty acid ester.

When the formulation of the present invention is a suspension, a liquid diluent such as water, ethanol or propylene glycol, a suspension agent such as ethoxylated isostearyl alcohol, polyoxyethylene sorbitol ester or polyoxyethylene sorbitan ester, microcrystalline cellulose, aluminum metahydroxide, bentonite, agar, tragacanth or the like may be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamide, vegetable oil, lanolin derivative or ethoxylated glycerol fatty acid ester may be used as a carrier component.

In the cosmetic composition of the present invention, the culture solution may be contained in an amount of 0.01 to 90 wt %, and preferably 3 to 15 wt %, based on the total weight of the composition, but is not limited thereto, so long as it is an effective amount suitable for providing the ability to increase the amount of *S. epidermidis*, to degrade histamine, to inhibit allergies, to repair DNA, and to increase wrinkle resistance, skin whiteness, skin density, and skin elasticity.

A better understanding of the present invention will be given through the following examples. These examples are merely set forth to illustrate the present invention and are not to be construed as limiting the scope of the present invention, as will be apparent to those skilled in the art.

<Example 1> Isolation of *Bifidobacterium* sp. GFC-B09 Strain 0.1 ml of a sample, obtained through extraction of the intestine from *Bombus pascuorum*, shaking in an MRS medium or a *Bifidobacterium* selective medium and then $10^4$-fold dilution (volume), was spread on an MRS agar medium (10 g of Peptospecial, 10 g of beef extract, 5 g of yeast extract, 20 g of glucose, 2 g of triammonium citrate, 5 g of sodium acetate, 0.2 g of magnesium sulfate, 0.05 g of manganese sulfate, 2 g of dipotassium phosphate, 15 g of agar, 1 g/L of Tween80, pH 6.2±0.2, MB cell (Cat. No. MB-M1025)), and was then cultured in an anaerobic incubator at 37° C. for 2 days. The resulting colonies were isolated and cultured, and single colonies formed after further culture in an anaerobic incubator for 24 hr were isolated. Among the isolated strains, a GFC-B09 strain having the ability to increase the amount of *S. epidermidis*, to degrade histamine, to inhibit allergies, to repair DNA, and to increase wrinkle resistance, skin whiteness, skin density, and skin elasticity was selected.

<Example 2> 16s rRNA Sequencing of Selected Strain

The GFC-B09 strain that was finally selected was identified to be a *Bifidobacterium* strain (SEQ ID NO: 3) through 16s DNA sequencing using gDNA thereof and SEQ ID NO: 1: 27F (5' AGA GTT TGA TCM TGG CTC AG 3') and SEQ ID NO: 2: 1492R (5' TAC GGY TAC CTT GTT ACG ACT T 3') as universal primers, and was named as a *Bifidobacterium animalis* subsp. *Lactis* GFC-B09 strain under the provisions of the Budapest Treaty on the International Recognition of the Deposit of Microorganisms for the Purposes of Patent Procedure, the GFC-B09 strain was deposited with the international depositary authority: the Korean Culture Center of Microorganisms (KCCM) on May 21, 2018 under the Accession Number: KCCM12263P.

<Example 3> Manufacture of Culture Solution of GFC-B09 Strain

The isolated GFC-B09 strain was seeded in an amount of 1% at $1.0 \times 10^9$ into an MRS medium. Thereafter, stationary culturing was carried out under anaerobic conditions at 37° C. for 120 hr. Thereafter, whether the pH was 4.0 (with a margin of 0.2) was confirmed, and when the culture solution was observed to be dark brown with the naked eye, culturing was completed, after which sterilization using a 0.2 μm filter (Millipore) was performed. After completion of filtration, aging at room temperature for 2 weeks was conducted, thus yielding a GFC-B09 strain culture solution.

<Example 4> Subject and Skin-Microbiome Sampling

This experiment was conducted on subjects who had provided prior consent through GFC Life Science Research Institute. As probiotics used for the experiment, the GFC-B09 strain culture solution was used, and after the culturing, the culture solution from which cells were removed was applied to the subject's facial skin, and skin samples were collected for a total of 72 hr and used for analysis. Here, a cotton swab method was used for collection, and skin samples were collected through scrubbing with gauze. The collected skin flora was divided into a pre-treatment group, a post-treatment group, an untreated (resting phase) group and a retreated group.

<Example 5> Genomic DNA Extraction and DNA Amplification of Skin Flora

The supernatant obtained by suspending the sample collected from the skin in 0.85% NaCl was centrifuged (17,000 rpm/m), and the resulting cells were washed once with a sterile saline, after which DNA was extracted therefrom using a FastDNA spin kit (MP Biomedical, France). In order to amplify the 16S ribosomal DNA gene of the extracted DNA, SEQ ID NO: 4: GC clamp (5'-CGCCCGGGGCGCGCCCCGGGCGGGGCGGGGGCACGGGGGG-3')-attached SEQ ID NO: 5: 341F (5'-CCTACGGGAGGCAGCAG-3') and SEQ ID NO: 6:518R (5'-ATTACCGCGGCTGCTGG-3') were used. For PCR reaction, 10 µl of Takara Perfect Premix (Takara, Japan) containing 0.4 mM dNTP, 0.5 units Taq polymerase and 4 mM $Mg^{2+}$ was added with 1 µl of DNA template (20 µg/ml), 1 µl of each of 1.0 µM forward primer and 1.0 M reverse primer, and the remainder of deionized water so that the total volume was 20 µl. A touchdown PCR method was carried out in a manner in which 2 cycles of amplification were performed each time while the temperature was lowered from 64° C. to 50° C. using C1000-Dual (Bio-Rad, USA), followed by treatment at 72° C. for 8 min and then storage at 4° C. The resulting PCR product was used for denaturing gradient gel electrophoresis (DGGE).

<Example 6> Denaturing Gradient Gel Electrophoresis (DGGE)

DGGE was performed using a D-code system (Bio-Rad, USA). The concentration of the polyacrylamide gel that was used was 8%, and a 40% polyacrylamide bis-solution 29:1 (3.3% C) (Bio-Rad, USA) was prepared to form a vertical concentration gradient ranging from 40% to 60%. The denaturant used was 7 M urea and 40% (w/v) formamide (Sigma, USA). The D-code system was filled with about 7 f of a TAE buffer (20 mM Tris, 10 mM acetic acid, 0.5 mM EDTA, pH 8.0), and 2× loading dye (0.05% bromophenol blue, 0.05% xylene cyanol, 70% glycerol) and the PCR product were mixed in the same amount, followed by electrophoresis at 50 V for 800 min. Thereafter, specific bands were analyzed after staining of the polyacrylamide gel with a RedSafe (Intron, Korea) solution for 15 min. The band intensity of the DGGE results was analyzed through image histogram and digitization using GelCompar2 (Bionumeric, Belgium).

As shown in FIG. 2, it was confirmed that the amount of *S. epidermidis*, which is skin flora beneficial for moisturizing activity, was increased depending on treatment with the GFC-B09 strain culture solution. Specifically, it was confirmed that, when the change rate in the amount of *S. epidermidis* in the pre-treatment group was set to 100%, the amount of *S. epidermidis* was increased to 610% upon treatment with the GFC-09 strain culture solution, was decreased to about 150% in the resting phase, and was increased again to 327% upon retreatment.

<Example 7> Histamine Reduction Effect

In order to evaluate the histamine reduction effect of the GFC-B09 strain culture solution obtained in Example 3, the activity of DAO (diamine oxidase) as a histamine-degrading enzyme was measured. Using a histamine enzyme immunoassay kit (SPI Bio, France) based on the principle of competitively binding labeled histamine and unlabeled histamine to antihistamine antibodies, the absorbance of the labeled histamine was measured at 405-414 nm, from which a reduction in the amount of histamine was confirmed. For a detailed method, the protocol in the corresponding kit was used.

Figure 3:
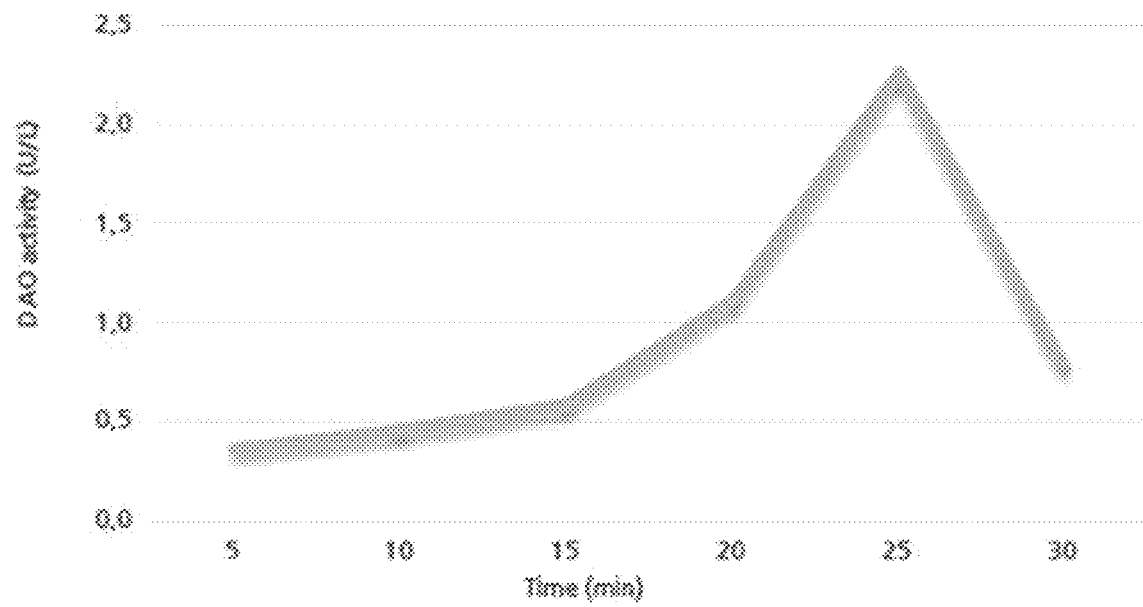
FIG. 3 is a graph showing the increased production of DAO enzyme by the culture solution of the *Bifidobacterium animalis* subsp. *Lactis* GFC-B09 strain (Accession number: KCCM 12263P) according to the present invention.

As shown in FIG. 3, the DAO activity was increased over time, and exhibited a maximum of 2.27 U/L (*unit definition: 1 Unit (U) of DAO catalyzes the conversion of 1 µmol of putrescine to pyrroline plus $NH_3$, and $H_2O_2$ in 1 min at pH 7.5), indicative of strong ability to degrade histamine.

<Example 8> Allergy Inhibition Effect: β-Hexosaminidase Inhibition Assay

In order to evaluate the effect of the GFC-B09 strain ferment obtained in Example 3 on inhibition of allergies, the inhibition of release of β-hexosaminidase, which is an allergic reaction indicator, was measured.

RBL-2H3 cells, a rat mast cell line, were cultured in a 5% $CO_2$ incubator at 37° C. using DMEM containing 10% fetal bovine serum and 1% penicillin/streptomycin. The RBL-2H3 cells thus cultured were aliquoted at $2.25 \times 10^5$ cells to each well of a 24-well plate, sensitized with 200 ng/ml of IgE, and cultured in a $CO_2$ incubator overnight. Thereafter, the cells were washed with a Siraganian buffer, treated with the sample dissolved in a Siraganian buffer and then cultured in a $CO_2$ incubator for 1 hr, followed by treatment with 50 ng/ml DNP-HSA, culturing in a $CO_2$ incubator for 1 hr 30 min and then collection of the supernatant. 50 µl of the supernatant thus collected and 50 µl of 5 mM p-nitrophenyl-N-acetyl-b-D-glucosaminide were cultured at 37° C. for 1 hr 30 min, after which the reaction was terminated with a 0.2 M citrate buffer, absorbance was measured at 405 nm, and the result was calculated using the following Equation 1.

β-Hexosaminidase inhibition rate (%)=(absorbance of group treated with test material/absorbance of group not treated with test material)×100     [Equation 1]

Figure 4:
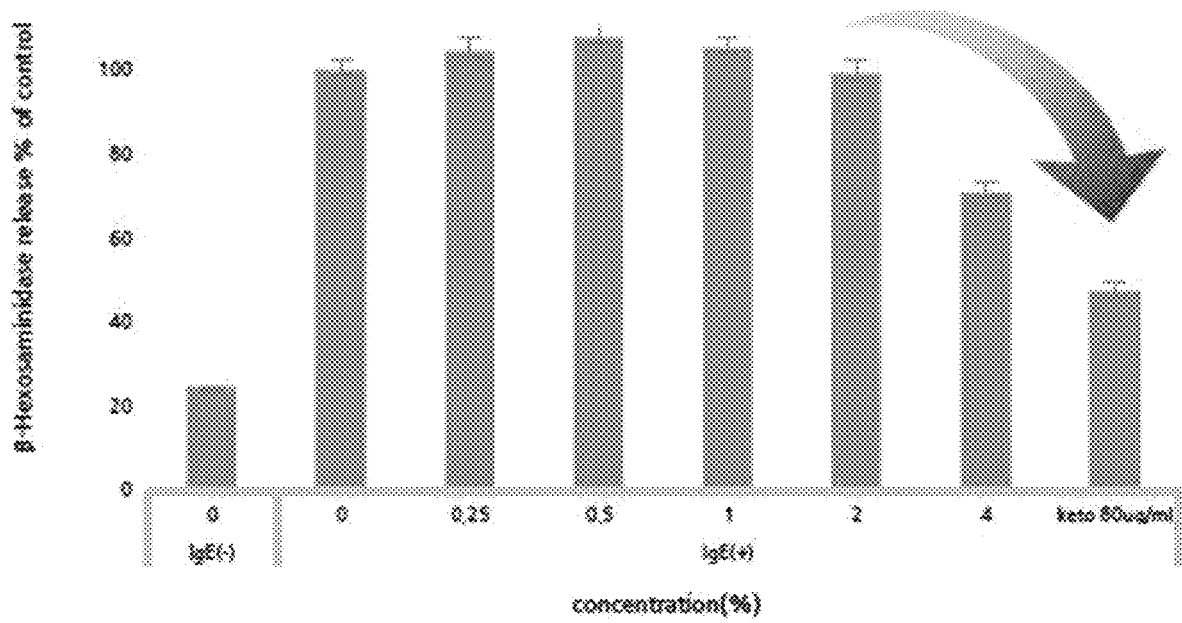
FIG. 4 is a graph showing the effect of the culture solution of the *Bifidobacterium animalis* subsp. *Lactis* GFC-B09 strain (Accession number: KCCM 12263P) according to the present invention on inhibiting 0-hexosaminidase.

As shown in FIG. 4, when treated with 4% GFC-B09 strain ferment, the release of (3-hexosaminidase, an allergic reaction indicator, was inhibited up to 30%, compared to the group not treated therewith, indicative of strong ability to inhibit allergies.

<Example 9> DNA Repair Effect

The DNA repair performance of the GFC-B09 strain ferment obtained in Example 3 was evaluated using a fluorescent microscope after cell staining.

As human-derived fibroblasts, human foreskin fibroblasts (hFFs) were cultured in a 5% $CO_2$ incubator at 37° C. using DMEM containing 10% fetal bovine serum (FBS) and 1% penicillin/streptomycin. The cultured hFFs were appropriately aliquoted to a 60 mm plate and cultured in a 5% $CO_2$ incubator at 37° C. and thus attached to the plate. After 24 hr, the medium was replaced with a serum-free medium containing no FBS, followed by culturing for 24 hr, damage to DNA through irradiation with UV at 40 mJ, and sample treatment, whereby the extent of repair of DNA upon sample treatment was compared with the group irradiated with UV and not subjected to sample treatment.

For DAPI (4,6-diamidino-2-phenylindole) staining and result analysis, the cells were immobilized for 10 min with 4% formalin, sufficiently washed with TBS-T, and stained with a DAPI dye, and the DNA repair was observed using a fluorescent microscope.

Figure 5:
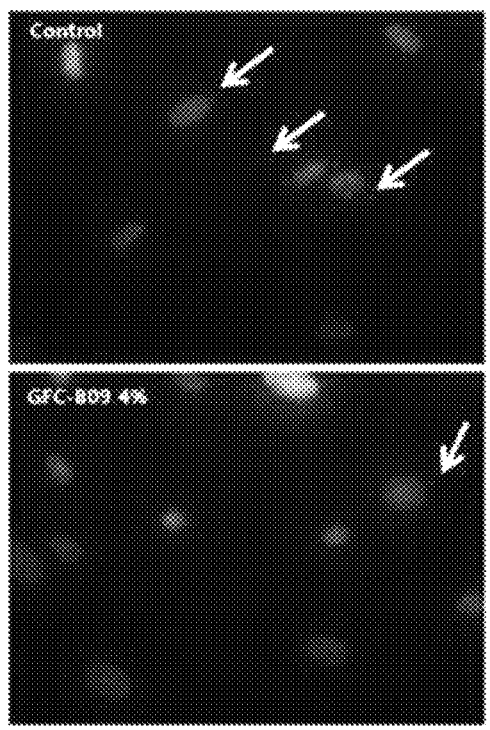
FIG. 5 is a graph showing the effect of the culture solution of the *Bifidobacterium animalis* subsp. *Lactis* GFC-B09 strain (Accession number: KCCM 12263P) according to the present invention on repairing DNA.
Figure 5:
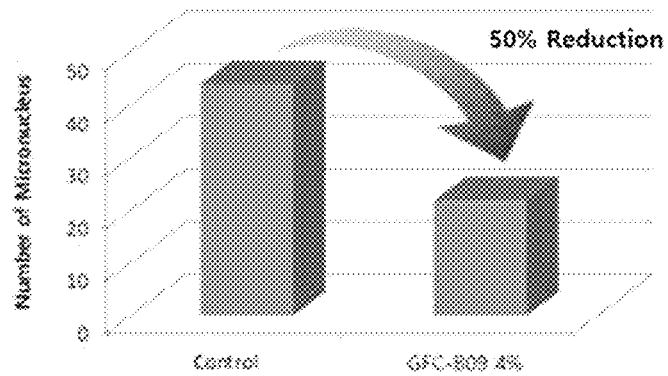

As shown in FIG. 5, upon treatment with the GFC-B09 strain ferment, it was confirmed that the damaged DNA was reduced by up to 50%, indicative of the ability to repair damaged DNA.

<Example 10> Clinical Trial

This clinical trial was conducted by the Korea Dermatology Research Institute under test number KDRI-2019-062 and IRB approval number KDRI-IRB-19062, and was faithfully conducted and implemented in accordance with the Korea Dermatology Research Institute's experimental regulations and Good Clinical Practice.

11 subjects were tested for a total of 4 weeks. For the test site using the sample, the eye wrinkle index and skin pigment index (M-value) decreased at a statistically significant level ($p<0.05$) starting 4 weeks after the use of the sample compared to before the use thereof, and moreover, skin density and epidermal elasticity increased, from which the test sample was found to be helpful for alleviating eye wrinkles, whitening the skin (hyperpigmentation reduction), and improving skin density and epidermal elasticity. Also, it was confirmed that the test material was safe because no special abnormalities occurred during the test period.

The detailed clinical trial methods are as follows.

1. Test Material Application Method

Subjects were trained according to instructions provided by the test sponsor in order to be identical to the actual usage. The test sponsor provided the following instructions: Take an appropriate amount in the morning and evening and apply gently over the entire face.

2. Test Sequence

1) First Visit

The use of basic skin care products is prohibited for 12 hr before the visit day.

Subjects are informed of the test method, schedule, risks and possible adverse events, and complete basic information, and sign a consent form.

After face washing with a standard cleanser provided by the test sponsor, pat drying with a paper towel to remove water and stabilization for 30 min under constant-temperature and constant-humidity conditions (20-24° C., 40-60% RH) are performed.

Facial photography is conducted using VISIA® CR, a high-resolution photography technology.

In order to carry out measurements at the same site for each evaluation, the measurement site is partitioned as follows and measurement using an instrument is performed.

a) Test site using Antera 3D

Square area having a size of 6 cm×6 cm, including the bilateral orbital and one eye rim b) Test site using Mexameter One spot on each side of the facial bilateral hyperpigmentation lesion c) Test site using ultrasound Position horizontally outwards 1 cm away from the lateral canthus d) Test site using cutometer Halfway position of imaginary line connecting the lip commissure and ipsilateral tragus The hyperpigmentation test site is visually evaluated by a dermatologist.

The subjects are provided with precautions and training on how to use the sample before the sample is distributed.

Compliance with regard to sample use is confirmed every day during the test period by telephone, etc.

2) Second Visit ($2^{nd}$ Week)/Third Visit ($4^{th}$ Week)

Facial photography and instrumental evaluation are performed in the same manner at the same site as the first visit.

The hyperpigmentation test site is visually evaluated by a dermatologist.

Subject's subjective evaluation of the hyperpigmentation test site is carried out.

The adverse events are evaluated by a dermatologist.

On the last visit, the sample is collected and the test fee is paid to the subjects.

Antera 3D-wrinkle index analysis is performed on the last visit when all images are taken in order to reduce measurement errors.

Evaluation and analysis method

1) Evaluation of Eye Wrinkle Alleviation Effect Using Antera 3D

Before the test, 2 weeks after the test, and 4 weeks after the test, the eye wrinkle index was measured.

The extent of eye wrinkle alleviation was obtained as a % value as follows.

Eye wrinkle alleviation rate (%)=measured value before test−measured value after test/measured value before test×100

2) Evaluation of Skin-Whitening (Hyperpigmentation Reduction) Effect Using Mexameter Before the test, 2 weeks after the test, and 4 weeks after the test, the skin pigment level was measured.

The extent of skin whitening (hyperpigmentation reduction) was obtained as a % value as follows.

Skin-whitening rate (hyperpigmentation reduction rate) (%)=measured value before test−measured value after test/measured value before test×100

3) Evaluation of Skin Density Improvement Effect Using Ultrasound

Before the test of the measurement site, 2 weeks after the test, and 4 weeks after the test, statistical significance between skin densities was analyzed and verified.

The extent of skin density improvement was obtained as a % value as follows.

Skin density improvement rate (%)=measured value before test−measured value after test/measured value before test×100

4) Evaluation of Elasticity Improvement Effect Using Cutometer

Before the test, 2 weeks after the test, and 4 weeks after the test, epidermal elasticity was measured using a cutometer.

The extent of elasticity improvement was obtained as a % value as follows.

Elasticity improvement rate (%)=measured value before test−measured value after test/measured value before test×100

5) Safety Evaluation by Dermatologist

During the test period, adverse events of sample use (erythema, swelling, scaling, itching, pain, burning, stiffness, tingling and other abnormalities) were evaluated.

3. Statistical Analysis Method

1) Significance was measured using MINITAB® 18, a statistical analysis software.

When the result value was estimated to be a normal distribution through the Ryan-Joiner Normality Test, significance was confirmed through the following parametric statistics.

Comparison of results before and after test within the same group: A paired t-test was used to compare the measured values before and after the test, and in the case of three or more repeated measurements, significance was confirmed at a significance level of $p<0.05$ through repeated measures ANOVA.

Comparison of results between two or more different groups: A Welch's t-test was used to compare the results between two groups, and for comparison of the results between three or more groups, significance was confirmed at a significance level of p<0.05 through one-way ANOVA.

Comparison of results of two or more different groups through repeated measurements: Significance was confirmed at a significance level of p<0.05 through repeated measures ANOVA, and when the initial measured values were significantly different between groups, the difference between groups was statistically confirmed through analysis of covariance using the initial measured values as covariates.

In the case of rejection of normality in the Ryan-Joiner Normality Test, significance was confirmed through the following nonparametric statistics.

Comparison of results before and after test within the same group: A Wilcoxon signed rank test was used to compare the measured values before and after the test, and in the case of three or more repeated measurements, significance was confirmed at a significance level of p<0.05 through a Friedman test.

Comparison of results between two or more different groups: A Mann-Whitney U test was used to compare the results between two groups, and for comparison of the results between three or more groups, significance was confirmed at a significance level of p<0.05 through a Kruskal-Wallis test.

Comparison of results of two or more different groups through repeated measurements: The difference between groups was statistically confirmed at a significance level of p<0.05 through a Friedman test.

In all data, continuous variables are summarized as mean and standard deviation, and categorical variables are summarized as frequency and percentage.

4. Test Results

[1] Eye Wrinkle Alleviation

Figure 6:
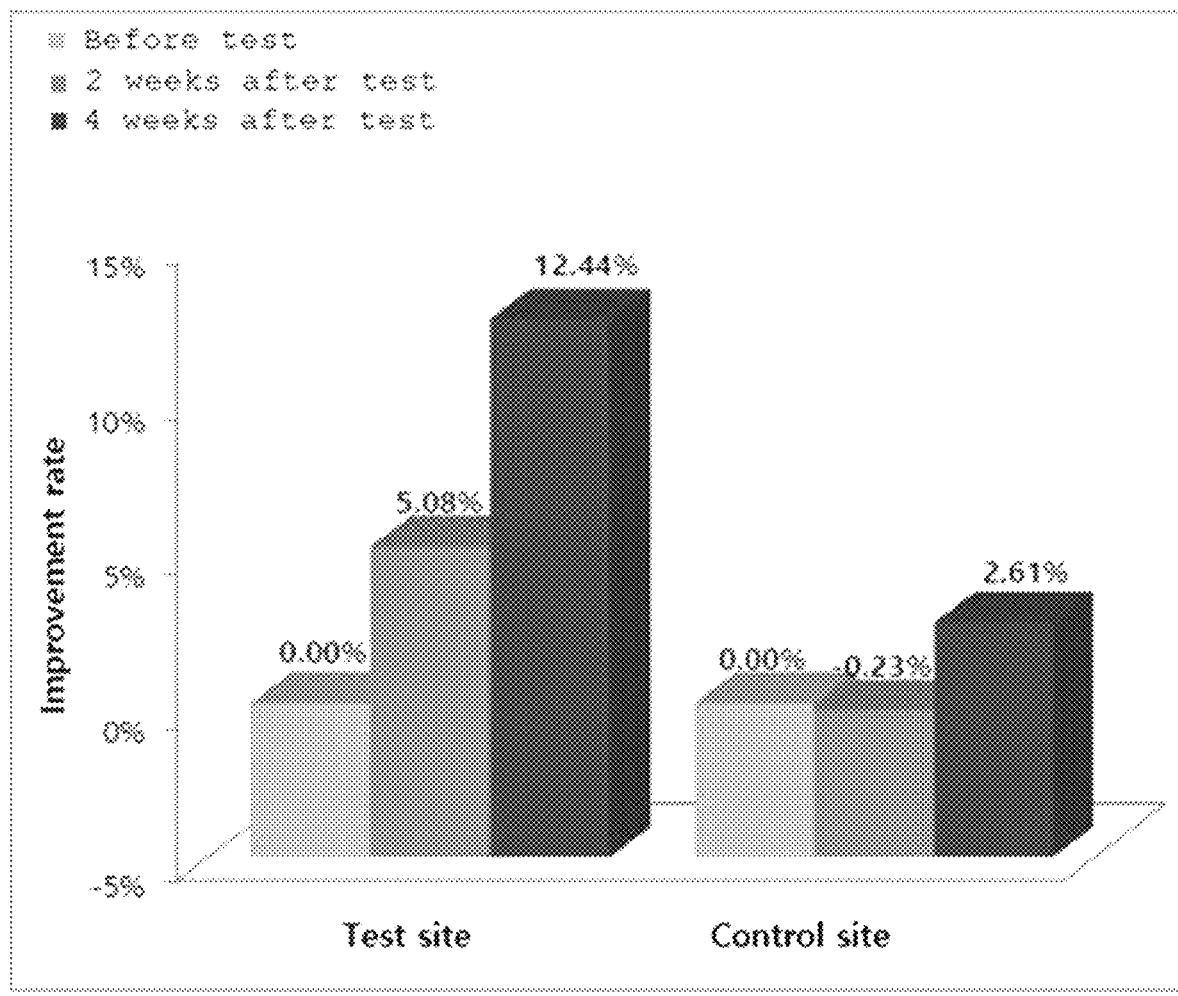
FIG. 6 is a graph showing the eye wrinkle alleviation rate after treatment of the skin with the culture solution of the *Bifidobacterium animalis* subsp. *Lactis* GFC-B09 strain (Accession number: KCCM 12263P) according to the present invention.

As shown in FIG. 6, the test site using the sample showed that the eye wrinkle index was reduced at a statistically significant level (p<0.05) starting 4 weeks after the test compared to before the test. However, the control site using the control sample showed no statistically significant change (p<0.05) compared to before the test.

The eye wrinkle index of the test site was determined using the indentation index of Antera 3D. The wrinkle alleviation rates at the test site and the control site were 5.08% and −0.23% 2 weeks after the test, and 12.44% and 2.61% 4 weeks after the test, respectively, indicating that the size of eye wrinkles at the test site was reduced.

[2] Skin Whitening

Figure 7:
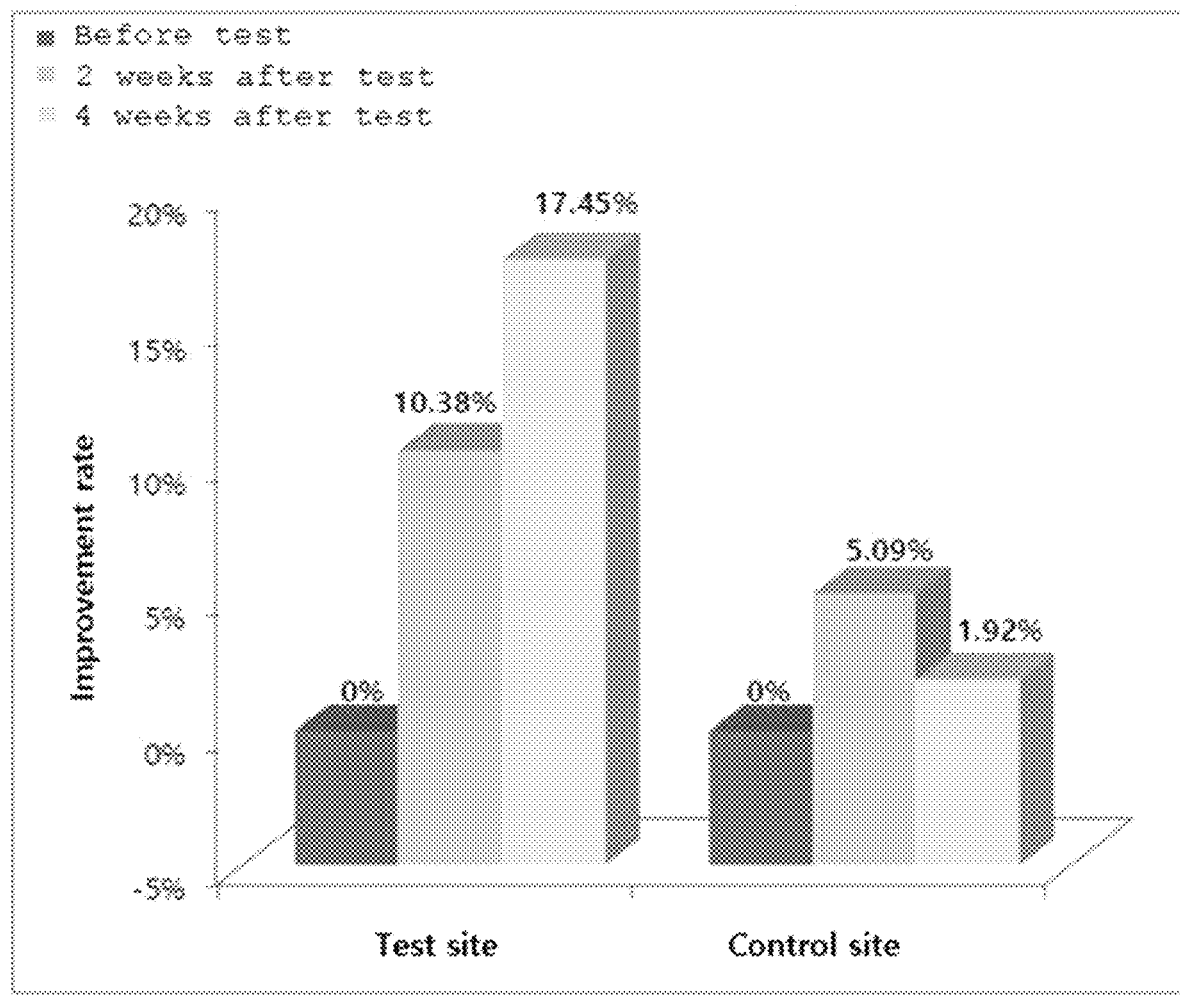
FIG. 7 is a graph showing the skin-whitening rate after treatment of the skin with the culture solution of the *Bifidobacterium animalis* subsp. *Lactis* GFC-B09 strain (Accession number: KCCM 12263P) according to the present invention.

As shown in FIG. 7, the test site using the sample showed that the skin pigment index (M-value) was decreased at a statistically significant level (p<0.05) starting 2 weeks after the test compared to before the test. However, the control site using the control sample showed no statistically significant change (p<0.05) compared to before the test. Moreover, based on the results of comparative control statistics between groups, a difference in the statistically significant level (p<0.05) between the test site and the control site was confirmed.

The whitening (hyperpigmentation reduction) of the test site was evaluated through instrumental evaluation, visual evaluation and subject's subjective evaluation.

Instrumental evaluation was performed using M-value measurement of Mexameter, and a total of five repeated measurements per site were carried out in order to increase the reliability of evaluation. Based on the evaluation results, the whitening rates at the test site and the control site were 10.38% and 5.09% 2 weeks after the test, and 17.45% and 1.92% 4 weeks after the test, respectively, indicating that the skin pigment index of the test site was lowered.

Visual evaluation was performed simultaneously by two skilled professionals including a dermatologist using a visual analog scale [0-9]. Here, if the evaluation values differed, the higher value was taken. Based on the evaluation results, neither the test site nor the control site showed any significant difference before or after the test, and there was no significant difference between groups.

Subject's subjective evaluation was performed on the $2^{nd}$ week and $4^{th}$ week following the test day. The extent of improvement of the test site and the control site was divided into three stages and evaluated. 11 subjects were judged to show improvement at the test site using the test sample in the $2^{nd}$ week, 9 subjects were judged to have show improvement at the test site in the $4^{th}$ week, 7 subjects were judged to show improvement at the control site using the control sample in the $2^{nd}$ week, and 10 subjects were judged to show improvement at the control site in the $4^{th}$ week.

[3] Skin Density Improvement

Figure 8:
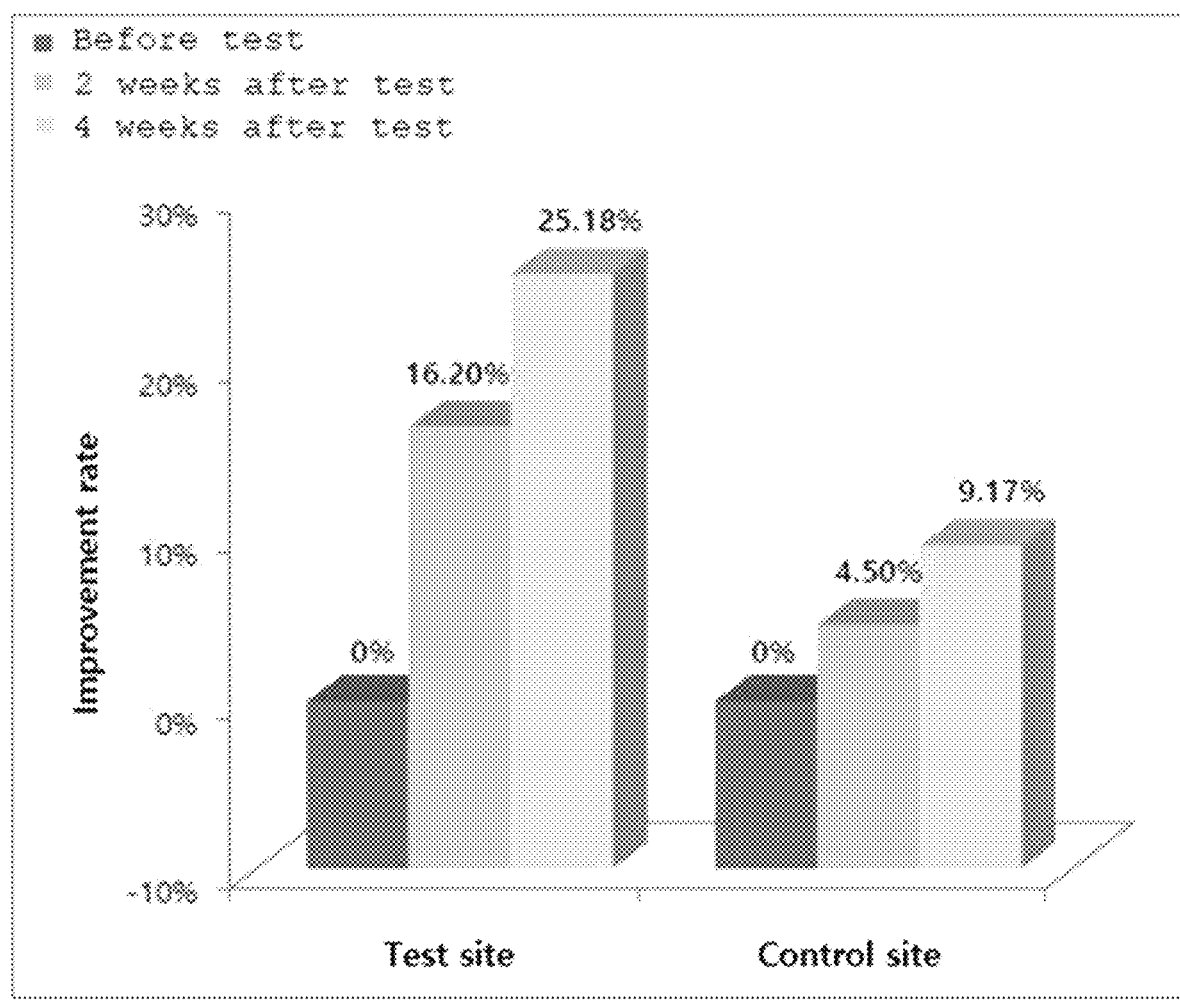
FIG. 8 is a graph showing the skin density improvement rate after treatment of the skin with the culture solution of the *Bifidobacterium animalis* subsp. *Lactis* GFC-B09 strain (Accession number: KCCM 12263P) according to the present invention.

As shown in FIG. 8, the skin density was increased at the test site using the test sample and the control site using the control sample at a statistically significant level (p<0.05) starting 2 weeks after the test compared to before the test. Based on the results of comparative control statistics between groups, a difference in the statistically significant level (p<0.05) between the test site and the control site was confirmed.

The dermal density improvement rates at the test site and the control site were 16.20% and 4.50% after 2 weeks of use compared to before the use of the sample, and 25.18% and 9.17% after 4 weeks of use, respectively. The skin density at the test site was increased at a statistically significant level (p<0.05) after using the test sample, indicating that the test sample had an effect of improving skin density.

[4] Skin Elasticity Improvement

Figure 9:
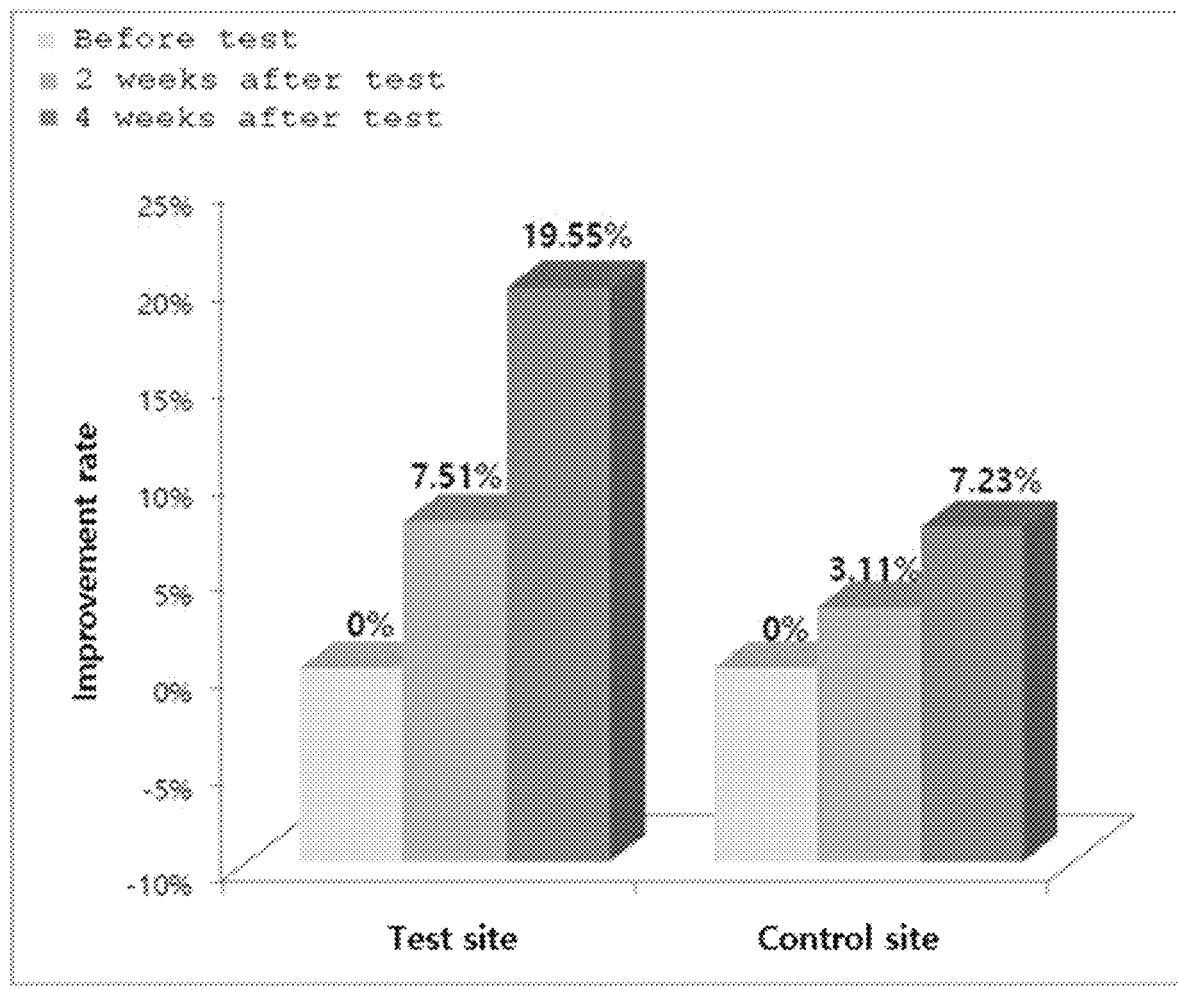
FIG. 9 is a graph showing the epidermal elasticity improvement rate after treatment of the skin with the culture solution of the *Bifidobacterium animalis* subsp. *Lactis* GFC-B09 strain (Accession number: KCCM 12263P) according to the present invention.

As shown in FIG. 9, the skin elasticity was increased at the test site using the test sample and the control site using the control sample at a statistically significant level (p<0.05) starting 4 weeks after the test compared to before the test. Based on the results of comparative control statistics between groups, a difference in the statistically significant level (p<0.05) between the test site and the control site was confirmed.

The improvement rates of R7 (Ur/Uf), which indicates skin elasticity, at the test site and the control site were 7.51% and 3.11% 2 weeks after the test, and 19.55% and 7.23% 4 weeks after the test, respectively, indicating that the epidermal elasticity of the test site was improved.

<Preparation Example 1> Preparation of Cosmetic Product Containing GFC-B09 Strain Culture Solution (1) Preparation of Skin Lotion A skin lotion was prepared through a typical method using the composition shown in Table 1 below.

TABLE 1

| Component | Amount (wt %) |
| --- | --- |
| Example 3 (GFC-B09 strain culture solution) | 3.00 |
| Hydroxyethylene cellulose (2% aqueous solution) | 12.00 |
| Xanthan gum (2% aqueous solution) | 2.00 |

TABLE 1-continued

| Component | Amount (wt %) |
| --- | --- |
| 1,3-Butylene glycol | 6.00 |
| Glycerin | 4.00 |
| Sodium hyaluronate (1% aqueous solution) | 5.00 |
| Purified water | 68.00 |
| Total | 100.00 |

(2) Preparation of Lotion

A lotion was prepared through a typical method using the composition shown in Table 2 below.

TABLE 2

| Component | Amount (wt %) |
| --- | --- |
| Example 3 (GFC-B09 strain culture solution) | 3.00 |
| Magnesium ascorbic acid-2-phosphate | 1.00 |
| Water-soluble collagen (1% aqueous solution) | 1.00 |
| Sodium citrate | 0.01 |
| Citric acid | 0.05 |
| 1,3-Butylene glycol | 3.00 |
| Purified water | 91.94 |
| Total | 100.0 |

While specific portions of the present invention have been described in detail, it will be understood by those skilled in the art that this specific technology is only a preferred embodiment, and that the scope of the present invention is not limited thereby. Therefore, the actual scope of the present invention will be defined by the appended claims and their equivalents.

ACCESSION NUMBER

Name of Depositary Authority: Korean Culture Center of Microorganisms (KCCM)
 Accession number: KCCM12263P
 Accession date: 20180521

What is claimed is:

1. A method of degrading histamine, reducing an amount of histamine, or repairing DNA, comprising administering an effective amount of a composition to a subject in need thereof, wherein the composition comprises a *Bifidobacterium animalis* subsp. *Lactis* GFC-B09 strain of Accession number: KCCM12263P.

2. The method of claim 1, wherein the composition is topically administered.

3. A method of increasing wrinkle resistance, skin whiteness, skin density, or skin elasticity, comprising administering an effective amount of a composition to a subject in need thereof, wherein the composition comprises a *Bifidobacterium animalis* subsp. *Lactis* GFC-B09 strain (Accession number: KCCM12263P).

4. The method of claim 3, wherein the composition is a cosmetic composition.

* * * * *